(12) United States Patent
Deladi et al.

(10) Patent No.: US 9,724,071 B2
(45) Date of Patent: Aug. 8, 2017

(54) DETECTION OF BIFURCATIONS USING TRACEABLE IMAGING DEVICE AND IMAGING TOOL

(75) Inventors: Szabolcs Deladi, Eindhoven (NL); Maya Barley, Eindhoven (NL); Niels Bakker, Eindhoven (NL); Drazenko Babic, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 439 days.

(21) Appl. No.: 13/825,865

(22) PCT Filed: Sep. 9, 2011

(86) PCT No.: PCT/IB2011/053952
§ 371 (c)(1),
(2), (4) Date: Mar. 25, 2013

(87) PCT Pub. No.: WO2012/042413
PCT Pub. Date: Apr. 5, 2012

(65) Prior Publication Data
US 2013/0303888 A1 Nov. 14, 2013

Related U.S. Application Data

(60) Provisional application No. 61/387,999, filed on Sep. 30, 2010.

(51) Int. Cl.
*A61B 8/14* (2006.01)
*A61B 8/00* (2006.01)
(Continued)

(52) U.S. Cl.
CPC ............ *A61B 8/4254* (2013.01); *A61B 5/066* (2013.01); *A61B 5/489* (2013.01); *A61B 8/085* (2013.01);
(Continued)

(58) Field of Classification Search
None
See application file for complete search history.

(56) References Cited

U.S. PATENT DOCUMENTS

| 5,617,878 A | 4/1997 | Taheri |
| 5,690,115 A | 11/1997 | Feldman et al. |

(Continued)

FOREIGN PATENT DOCUMENTS

| JP | 2008142330 A | 6/2008 |
| JP | 2010148778 A | 7/2010 |

OTHER PUBLICATIONS

Y. Sun et al., "Image Guidance of Intracardiac Ultrasound With Fusion of Pre-Operative Images", MICCAI 2007, Part I, LNCS 4791, pp. 60-67.

*Primary Examiner* — James Kish

(57) ABSTRACT

A system, device and method include an interventional device having at least one ultrasonic transducer configured to generate a signal to indicate presence of a branch or bifurcation of a lumen inside a subject. A localization system is configured to track the interventional device in the subject. A program module is implemented by a processor to compare a position of the interventional device against a reference image and to indicate the presence of the branch or bifurcation relative to the interventional device position in accordance with the signal.

20 Claims, 8 Drawing Sheets

(51) Int. Cl.
    *A61B 5/06*      (2006.01)
    *A61B 5/00*      (2006.01)
    *A61B 8/08*      (2006.01)
    *A61B 8/12*      (2006.01)
    *A61B 34/20*     (2016.01)
    *A61B 6/12*      (2006.01)
    *A61B 90/00*     (2016.01)

(52) U.S. Cl.
    CPC .............. *A61B 8/0891* (2013.01); *A61B 8/12* (2013.01); *A61B 8/445* (2013.01); *A61B 34/20* (2016.02); *A61B 6/12* (2013.01); *A61B 2034/2051* (2016.02); *A61B 2090/378* (2016.02)

(56) References Cited

U.S. PATENT DOCUMENTS

| | | |
|---|---|---|
| 6,102,938 A | 8/2000 | Evans et al. |
| 2004/0148006 A1 | 7/2004 | Davidson et al. |
| 2004/0167619 A1 | 8/2004 | Case et al. |
| 2005/0038343 A1* | 2/2005 | Cao .................. A61B 8/06 600/454 |
| 2005/0209669 A1 | 9/2005 | Kao |
| 2006/0241465 A1* | 10/2006 | Huennekens et al. ........ 600/458 |
| 2007/0015996 A1 | 1/2007 | Camus et al. |
| 2007/0016068 A1 | 1/2007 | Grunwald et al. |
| 2007/0208256 A1 | 9/2007 | Marilla |
| 2007/0244394 A1 | 10/2007 | Greenan |
| 2008/0004530 A1 | 1/2008 | Feldman et al. |
| 2008/0085042 A1 | 4/2008 | Trofimov et al. |
| 2008/0140180 A1 | 6/2008 | Dolan et al. |
| 2008/0171934 A1 | 7/2008 | Greenan et al. |
| 2008/0199059 A1 | 8/2008 | Eck et al. |
| 2008/0283771 A1 | 11/2008 | Li |
| 2009/0228020 A1 | 9/2009 | Wallace et al. |
| 2010/0063400 A1 | 3/2010 | Hall et al. |
| 2010/0076317 A1 | 3/2010 | Babic et al. |

* cited by examiner

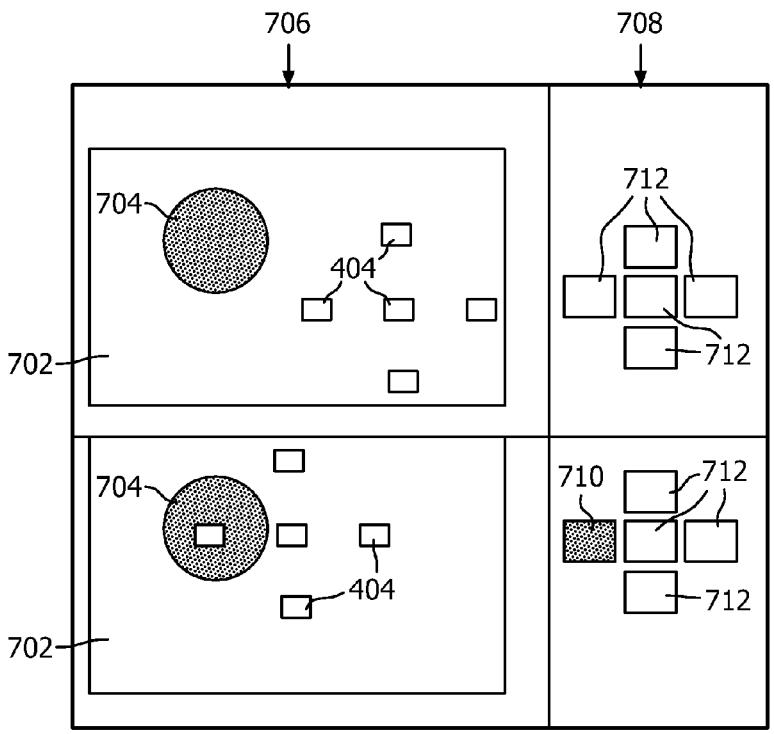
FIG. 7A
FIG. 7B
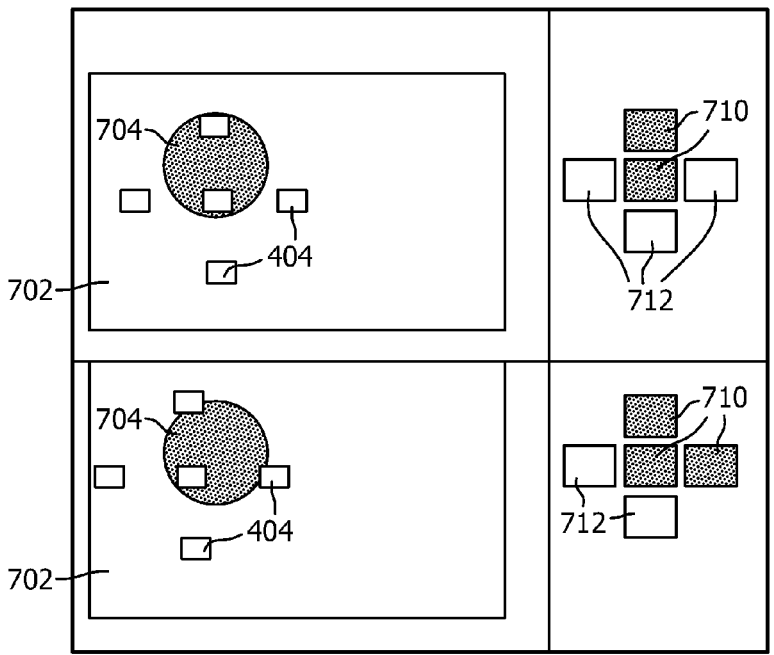
FIG. 7C
FIG. 7D

DETECTION OF BIFURCATIONS USING TRACEABLE IMAGING DEVICE AND IMAGING TOOL

This disclosure relates to detection of internal organ structures, and more particularly to systems and methods for detecting bifurcating structures, such as blood vessels, and integrating side-branch information for guidance of interventional tools and procedures.

Abdominal aortic aneurysms (AAA) are a weakening and bulging of the aortic wall. This condition is the third leading cause of sudden-death in men over 65 in the US, and affects 2-3 million people in the US alone. Currently, the treatment option with the lowest associated morbidity and mortality is endovascular repair, in which a bifurcated, covered stent-graft is delivered via a catheter under fluoroscopic guidance to within the AAA sac.

In order to place such a stent-graft safely and securely, the aneurysm must have a sufficiently long 'neck' (the distance between the ends of the aneurysm sac and the nearest critical side-branch arteries of the aorta, such as the renal and internal iliacs) so that the stent-graft can be implanted securely without risk of obstructing blood flow to these important side-branch vessels. It is estimated that in more than 30% of patients, the aneurysm neck is not long enough to safely and securely place a standard stent-graft. These patients may then either undergo open surgery (which may increase risk) or receive a custom-made pre-fenestrated stent-graft (which is highly expensive and may take upwards of 6 months to manufacture, during which time risk of rupture of the patient's aneurysm persists).

In-situ stent-graft fenestration, in which the stent-graft is punctured in the correct locations to allow continuing blood flow to critical side branch arteries, is a method that promises to bring cost-effective and immediate minimally-invasive treatment to the remaining 30% of patients. In this procedure, the stent-graft is placed in a standard way, and then fenestrated with a needle or cutting balloon at the correct locations.

Discovering the puncture sites and branching blood vessel location is a difficult task. In the minimally-invasive treatment as described above or even for other procedures, e.g., oncology, cardiac arrhythmias and valve repairs, thin devices are used such as needles and catheters. Other minimally-invasive treatments employ sheath-like devices for introduction of treatment devices, such as deploying stents in blood vessels. The size of the treatment and monitoring device is important, since it is usually limited by its pathway (blood vessels, etc.) and related directly to the post-operative trauma. The diameter restrictions (for catheters and needles) or the wall thickness (for sheets) are responsible for many limitations in surgical procedures.

In accordance with the present principles, systems, devices and methods are disclosed which provide a combination of ultrasound imaging with discrete ultrasound transducers and fluoroscopy information. Important internal structures for an interventional procedure (e.g. blood vessel branches) can be found with greater accuracy. One advantage reduces electronics in the already limited sized devices. In one embodiment, a minimally-invasive device combines diagnosis, navigation and treatment possibilities.

A system, device and method include an interventional device including one or more ultrasonic transducers configured to generate a signal to indicate presence of a branch or bifurcation of a lumen inside a subject. A localization system is configured to track the interventional device in the subject. A program module is implemented by a processor to compare a position of the interventional device against a reference image and to indicate the presence of the branch or bifurcation relative to the position in accordance with the signal.

An interventional device includes an elongated body having a tip, and a localization device mounted in the tip for determining a position of the tip during a procedure. An ultrasonic transducer is mounted on or in the elongated body and is configured to output a signal to indicate if a branch or bifurcation is present within a lumen and, if present, a position of the branch or bifurcation is determined by a position of the tip as provided by the localization device.

A method for determining branching or bifurcation of an internal structure includes determining a position of an interventional device in a main lumen using a localization system; outputting ultrasonic signals from the interventional device to construct an ultrasound image of the lumen; determining a presence and position of a branch or bifurcation relative to the interventional device using ultrasound signals; and indicating the branches or bifurcations in a reference image.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein:

FIGS. 7A-7D show an internal event within a subject where one or more transducers overlap a branch and further show an output display corresponding to the event in accordance with an illustrative embodiment;

Figure 1:
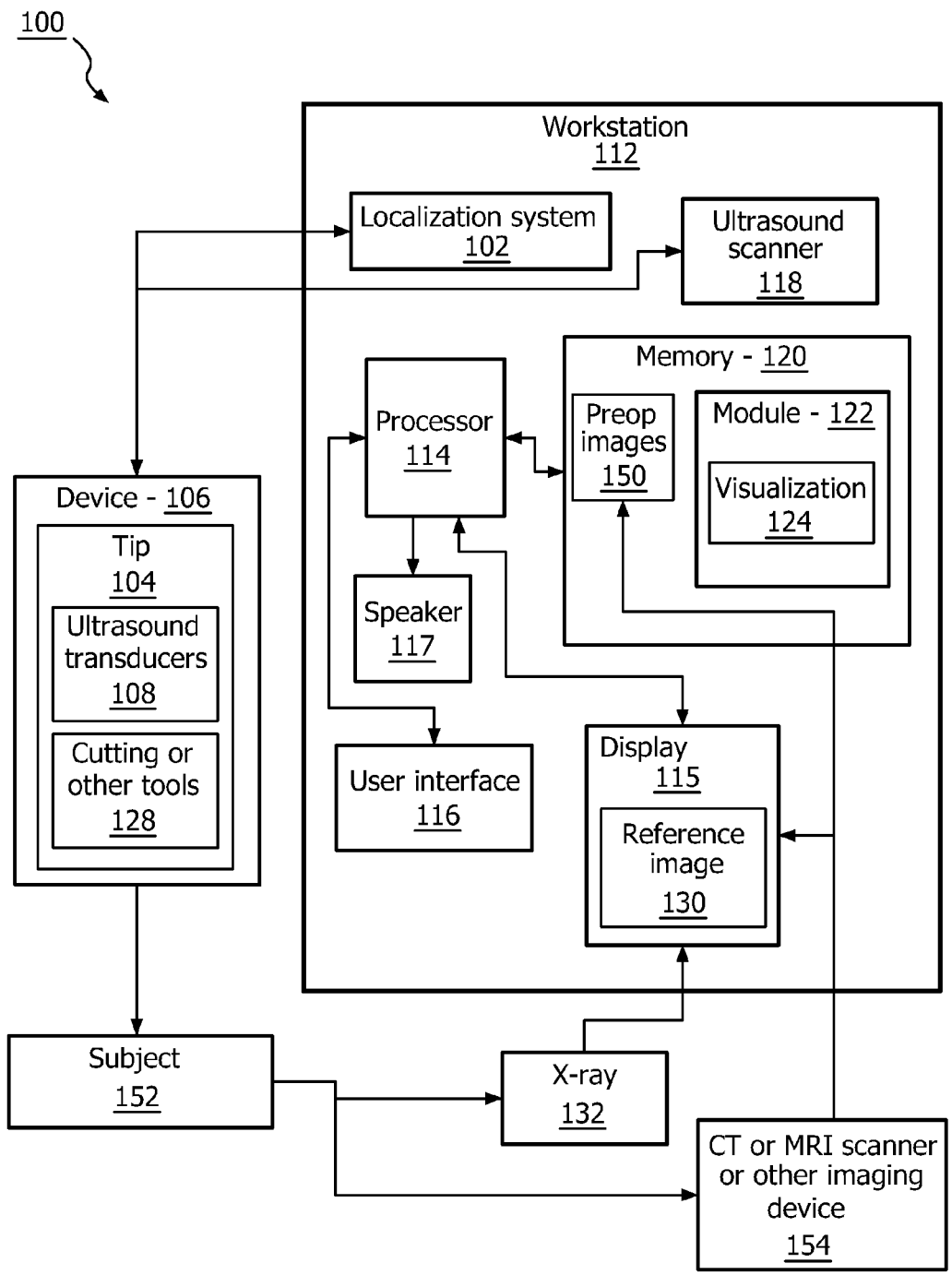
FIG. 1 is a block/flow diagram showing an illustrative system/method for locating branches in a lumen and displaying a patent status of the branches in accordance with one embodiment.

The present principles provide systems, devices and methods for performing interventional procedures which locate and operate on internal organs. In one embodiment, a plurality of discrete ultrasound transducers is mounted on a minimally invasive device to assist in finding back critical structures such as blood vessel branches. The interventional device is preferably traceable in a fluoroscopy image or other real-time image, and a position of the device can be registered with pre-procedural information (e.g., computer tomography (CT) images, magnetic resonance images (MRI), etc.).

In one embodiment, a cutting tool may be included with the interventional device. The cutting tool may be employed to perform stent-graft fenestration simultaneously when side-branch locations of a blood vessel are identified. The cutting tool permits physicians to create fenestrations safely and effectively and provides a seamless integration with current visualization platforms.

Structures such as blood vessel branches are difficult to find without local imaging modalities embedded in minimally invasive devices. In one embodiment, visualization need not be at the intravenous ultrasound level (IVUS-level), although a detailed visualization is beneficial. Side-branch arteries may be at about 2-3 mm in diameter, therefore 0.2 mm resolution (as provided by IVUS for tissue characterization) is not necessary. However, such resolution may be employed for smaller blood vessels or other organs.

It should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, a localization/visualization system 100 is illustratively shown in accordance with one embodiment. The system 100 includes a localization system 102 capable of localizing (identifying a position of) a tip 104 of an ultrasonic-imaging device 106. The localization system 102 may include one or more of electromagnetic (EM) tracking, magnetic resonance (MR) localization, Fiber Bragg Grating (FBG) tracking, direct image processing of an X-ray image, etc. The device 106, which may include a needle, a catheter or other interventional device includes the tip 104, which can be localized with high accuracy in real-time using the localization system or systems 102. The device 106 may include other tools and devices, such as a cutting tool or balloon 128, lights, cameras, etc.

System 100 may include a work station 112. The workstation 112 may include a computer processor 114, a display 115, a user interface 116 (e.g., mouse, keyboard, etc.), an ultrasonic or other type scanner 118 (which may be coupled to the device 106) and memory 120 for storing data and software. Memory 120 may store preoperative images 150 and map volumes of a subject 152 taken using imaging devices 154 such as CT, MRI or other imaging devices.

The software may include a module 122 configured to determine the presence or absence of an anatomical feature needed to perform a particular procedure. In one embodiment, module 122 determines a position/location of a side-branch artery, e.g., by using low-resolution ultrasonic imaging from at least one ultrasound-imaging unit 108 at the tip 104 of device 106 that can detect whether there is a hole (e.g., an arterial opening) in the wall of a blood vessel during a procedure. In an alternate embodiment, an array of ultrasonic transducers is provided to locate the position/location of the side-branch artery.

Module 122 preferably works in conjunction with images on the display 115. A reference image 130 may be generated using real-time images taken of the subject 152 or may include preoperative images 150. The real-time image may be taken using an X-ray machine or source 132. The device 106 is localized by localization system 102 and its position (e.g., tip 104) is displayed in real-time. Module 122 may indicate on display 115, bifurcation and other structures discovered during the procedure.

In one embodiment, a visualization system 124 is included in module 122 which permits a position of the side-branch to be overlaid on a fluoroscopy screen. During an endovascular repair procedure, whether a side-branch is covered by a stent-graft or not is indicated by a property of the overlaid image. In one embodiment, this property may include a color indicator for the overlaid side-branch image. Side-branches covered by the stent-graft are shown in one color, while those that remain patent (with continuing blood flow) are shown in another. In another embodiment, acoustic feedback may be rendered in addition to or instead of a visual indicator using a speaker 117 to indicate blood flow status of the side-branches. The speaker 117 can provide a tone in accordance with the amount and direction of blood flow in the side-branch(es). The audible sound is preferably based on the Doppler effect. Flow conditions for an ultrasonic flow-meter using transducers 108 are very favorable since the blood will stream flow towards or away from the transducer 108, thus the frequency shift can be quite large.

Module 122 interprets a position of the device 106 and any instruments or appliances carried by the device 106 using the localization system 102. The module 122 also includes a detailed image of the internal structure using the ultrasonic capabilities (108) of the device 106. These two are combined with preoperative images (e.g., fluoroscopic images, CT images, MR images, etc.) to indicate relative positions, e.g., a position of a stent-graft or the like. Indicators (e.g., colors) are based upon conditions monitored by module 122. Information is updated in real-time as the stent-graft is punctured and blood flow resumes (e.g., the color of the overlaid image changes).

In accordance with the present principles, physicians are provided with a tool that will display vessel-coverage status in real-time to permit the physicians to determine which side-branches need to be treated, and where the side-branches are located. This increases the efficiency and efficacy with which stent-graft fenestration is conducted, and reduces the risk of patient complications. The vessel patency information is displayed in such a way that it blends seamlessly with the standard visualization system (i.e., no extra displays are needed). Furthermore, the system 100 does not disturb current clinical workflow, since the patency information is displayed exactly at the location on the image at which physicians will normally be focused during stent-graft fenestration (i.e. on the real-time image of the device tip 104 within the blood vessel).

Figure 2:
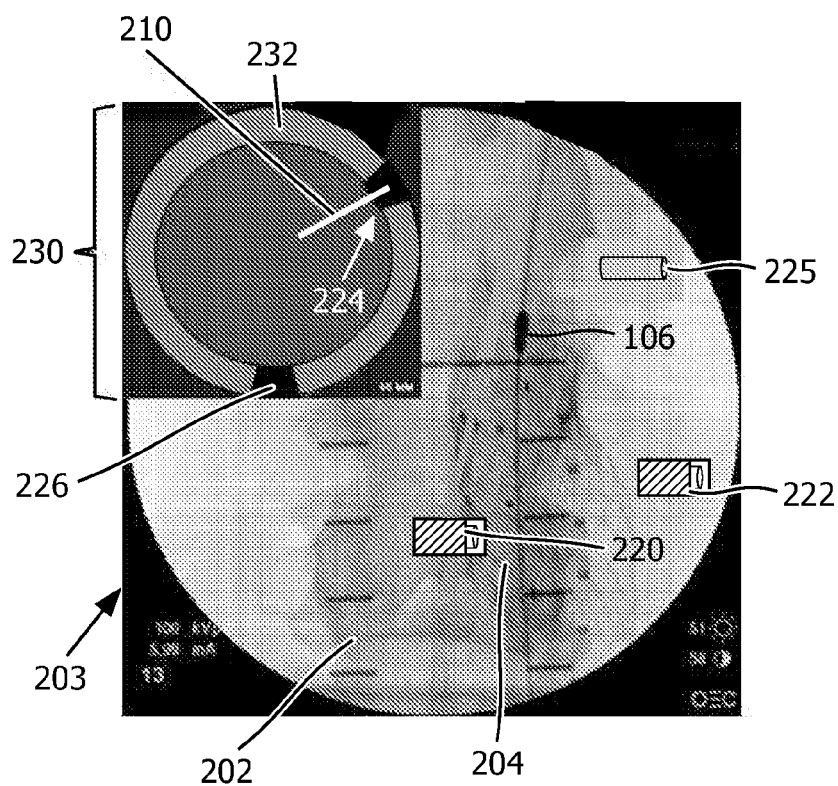
FIG. 2 is a reference image showing an X-ray updated in real-time with indicators of patent status and branch locations in accordance with one illustrative embodiment.

Referring to FIG. 2 with continued reference to FIG. 1, a display image 202 illustratively shows how ultrasonic imaging information is integrated on a fluoroscopy display 203 to indicate side-branch vessel patency using the visualization system 124. In this embodiment, side-branches 220, 222 covered by a stent-graft 204 are indicated in a first color (e.g., red), while side-branches 225 that remain patent (with continuing blood flow) are shown in a second color (e.g., green). In FIG. 2, the color red is indicated by hatch marks and green is clear. It should be understood that colors may be replaced by textures, shading or other visual effects. In addition, audible feedback may be provided to the physician to indicate the patency of the side-branches.

The physician can deliver the stent-graft 204 with a standard technique, and then do a quick 'pull-back' of the device 106 so that the localization system 102 and the ultrasonic device 108 may be employed by module 122 to determine which side-branch arteries are covered by the stent-graft, and which remain patent. This information is automatically displayed on the fluoroscopy screen 203.

Figure 3:
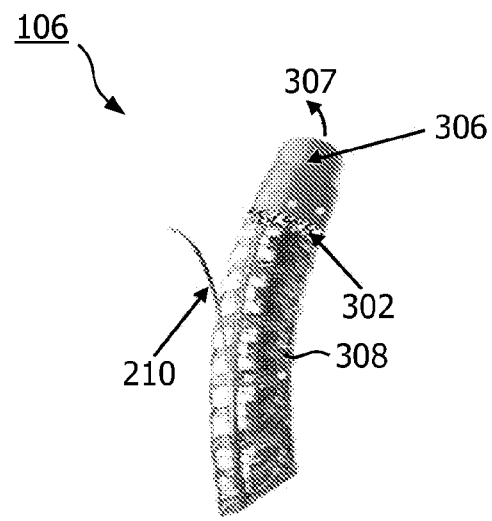
FIG. 3 is a perspective view of an interventional device including a cutting tool, localization device and ultrasonic transducers in accordance with an illustrative embodiment.

In one embodiment, device 106 can also assist in treatment planning since some vessels need to be prioritized for treatment (e.g., the renal arteries), while others do not need to be fenestrated (such as the inferior mesenteric). Device 106 may be equipped with a cutting tool 210 (in this case a guidewire with a needle tip) that can then be used to fenestrate the stent-graft 204 at a correct location. This cutting tool 210 can either be separate from the device 106, or integrated as shown in FIG. 3.

Other images 230 may be generated to provide additional information to the physician. A cross-sectional view of a blood vessel 232 from side-looking imaging can be displayed in a simple way (also on the fluoroscopy screen 203) to indicate branch openings, device 106 location, cutter 210 location, etc.

It should be understood that stents may be employed that include openings for branching blood vessels. Imaging through the stent-graft may be useful in placing branched stent-grafts (where the stent-graft has side-branch stents already built into the device). One challenge for the physician is to thread guidewires quickly and with minimum contrast usage through the side-branch stents and into the side-vessels before the device can be fully deployed. Imaging integrated into the deployment device could provide real-time feedback on the locations of the side-vessels with respect to the side-branches, and thus assist with guidewire introduction.

Device-based imaging could also be useful in placing pre-fenestrated stent-grafts (similar to branched stent-grafts, except with holes in place of side-branches). As before, the challenge is to thread guidewires quickly and with minimum contrast through these holes and into the relevant side-vessels before the device can be fully deployed. Side-looking imaging, as described herein, provides a very useful tool to see through the stent-graft and identify the side-vessels through the stent-graft holes and precisely and quickly insert guidewires into these side-vessels. These applications would benefit greatly by employing the present principles. Other applications that would benefit may include, e.g., cases where an aneurysm 'neck' is very short and placement must be very accurate, when multiple, overlapping stents need to be deployed along the aorta or other vessel.

Referring to FIG. 3, an illustrative example of the device 106 having integrated imaging (e.g., ultrasound transducer elements 302) and a cutting tool 210 are shown. Elements 302 may include annular side-looking elements which provide cost effective low-resolution ultrasound imaging for side-branch vessel localization and cutting-tool positioning. Device 106 may include a retractable, steerable guidewire with a Brockenbrough needle or cutting balloon as a cutting tool 210. The device 106 may include a sheath or cover 306 on a catheter body 308 which may include a perforation(s) 307 to dispense contrast or provide other functions. A localization device (e.g., 406) is mounted within the catheter body 308.

Intravenous ultrasound (IVUS) is usually a high-resolution side-looking imaging modality that provides a cross-sectional view of the vessel contents and tissue in the vessel wall. Such resolution may be beneficial for some embodiments; however, to provide information on side-branch vessel location, only low-resolution imaging is in principle needed (the physician simply needs to know if a side-branch vessel is "there or not"). (See image 230 of FIG. 2).

Referring again to FIG. 2, unlike with IVUS, only a low resolution image is needed. Image 230 provides the physician a cross-sectional profile of a blood vessel 232, such as an aorta at the real-time location along the aorta length at which the device 106 is positioned. The image 230 also indicates ostia of the side-branch vessels indicated by a segmental cut-out 224. A segment 226 indicates that a side-branch vessel has been detected but is just out of the imaging plane of the annular ring of elements 302 (FIG. 3). An image of the cutting tool 210 may also be shown on image 230, to assist with positioning of the cutting tool 210 on the stent-graft adjacent to the side-branch ostium.

Figure 4A:
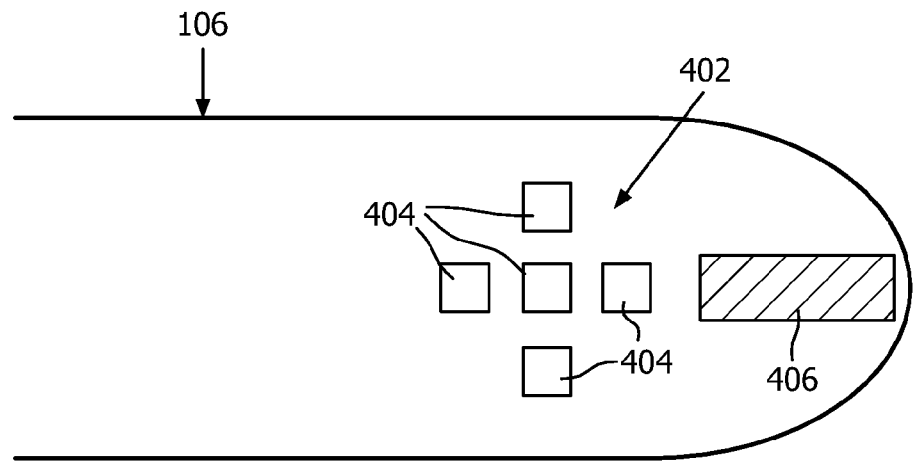
FIGS. 4A and 4B show cross-sectional views of a catheter and a sheath respectively having an electromagnetic position tracking device and an array of ultrasonic transducers in accordance with one illustrative embodiment.
Figure 4B:
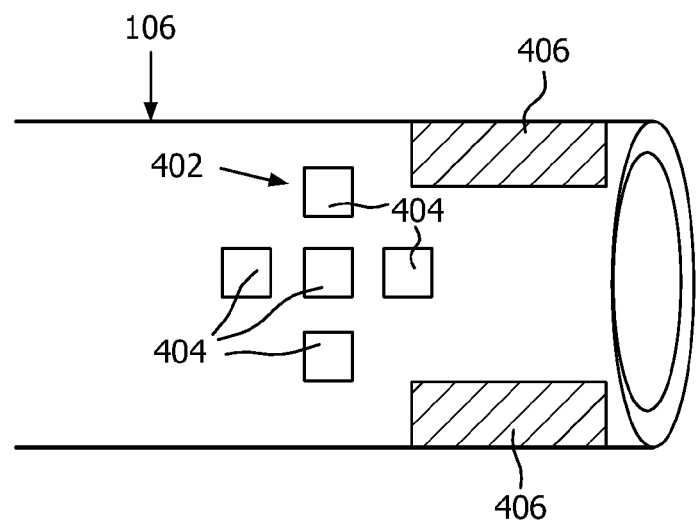

Referring to FIGS. 4A and 4B, another embodiment of device 106 is equipped with an array 402 of ultrasonic transducers 404. In FIGS. 4A and 4B, two different embodiments of device 106 include a closed end catheter (FIG. 4A) and an open end sheath (FIG. 4B). Each device 106 includes a plurality of discrete ultrasound transducers 404 arranged in an array 402 and one or more EM tracking coils 406. The number of transducers 404 and/or the number of coils 406 may change as needed or desired. The device 106 (e.g., catheter/sheath) preferably includes a working channel for intervention (stent perforation, cutting tool, ablation, contrast injection, etc.), pressure sensors, temperature and electrical signal sensors, ablation electrodes, etc.

Figure 5A:
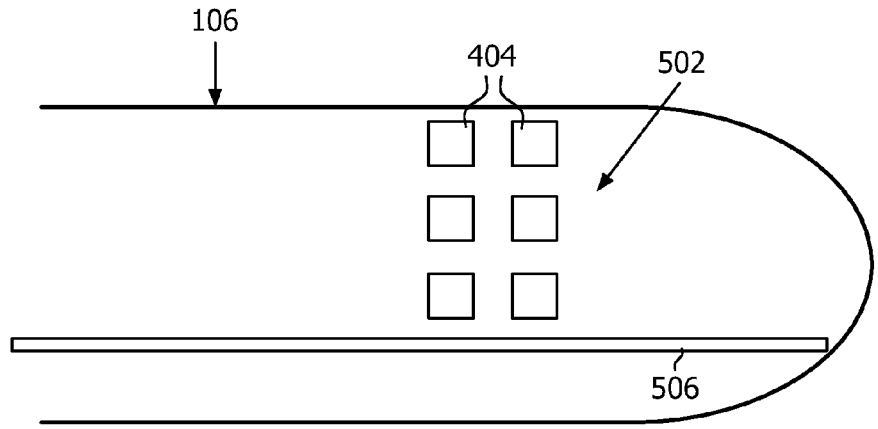
FIGS. 5A and 5B show cross-sectional views of a catheter and a sheath respectively having an optical fiber position tracking device and an array or ultrasonic transducers in accordance with another illustrative embodiment.
Figure 5B:
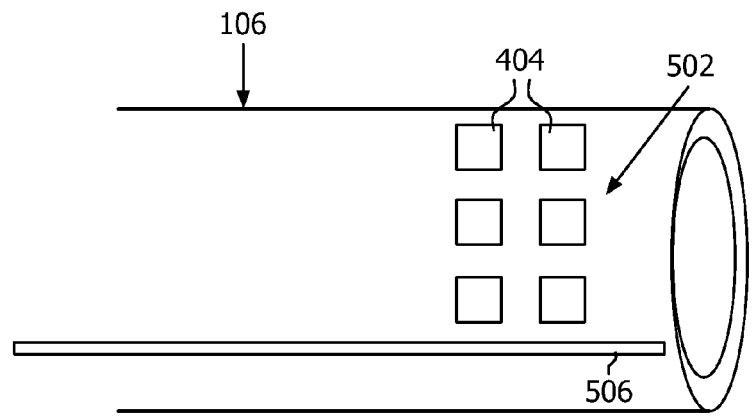

Referring to FIGS. 5A and 5B, another embodiment of device 106 is also equipped with an array 502 of ultrasonic transducers 404. In FIGS. 5A and 5B, two different embodiments of device 106 include a closed end catheter (FIG. 5A) and an open end sheath (FIG. 5B). Each device 106 includes a plurality of discrete ultrasound transducers 404 arranged in an array 502 and one or more fiber tracking sensors/fibers 506. The fiber tracking sensors may include Fiber Bragg Gratings or the like. The number of transducers 404 and/or the number of sensors/fibers 506 may change as needed or desired. The device 106 (e.g., catheter/sheath) preferably includes a working channel for intervention (stent perforation, cutting tool, ablation, contrast injection, etc.), pressure sensors, temperature and electrical signal sensors, ablation electrodes, etc.

Figure 6:
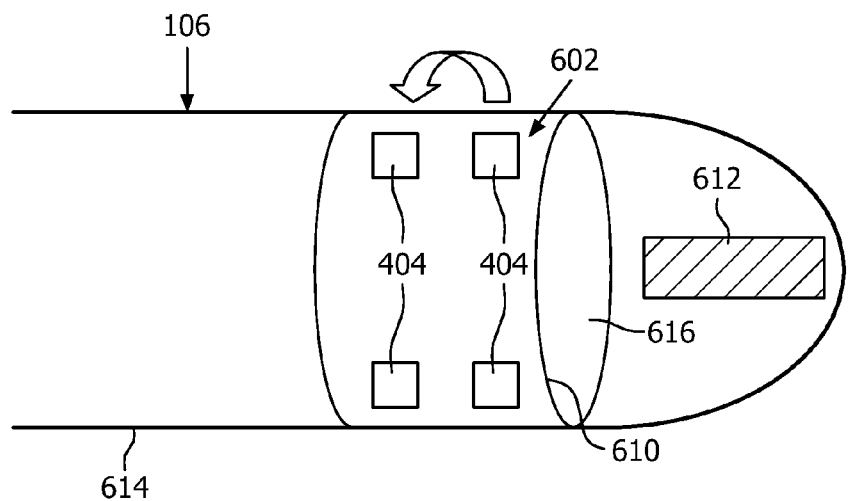
FIG. 6 shows a cross-sectional view of a catheter (or a sheath) having a rotating cylinder for mounting ultrasonic transducers and a tracking device in accordance with yet another illustrative embodiment.

Referring to FIG. 6, yet another embodiment of device 106 is also equipped with an array 602 of ultrasonic transducers 404 mounted on or in a rotating annular cylinder 610. In this embodiment, device 106 includes a catheter with discrete ultrasound transducers 404 and an EM tracking coil 612. The transducers 404 are mounted onto the annular cylinder 610 in a coaxial relationship with the catheter, and can be rotated with respect to a catheter body 614. Rotation may be provided using a wire or using a motor or servo at the distal end portion of the device. In this way, translation of the catheter (or any other motion) can be combined with the rotation of the annular cylinder 610 with the ultrasound transducers 404. The annular cylinder 610 can be placed on the outside of the catheter, or inside a chamber 616 within the catheter body 614. The chamber 616 can be open, or closed. In case the chamber 616 is closed, then acoustical contact between the ultrasound transducers 404 on the annular cylinder 610 and an outside medium (e.g., blood in a stenting process, tissue in cardiac ablation, etc.) is mediated by saline solution that can be dispensed via irrigation tubing within the catheter body 614. The chamber 616 can be closed by acoustically transparent plastic, e.g., Polymethylpentene, Pebax or the like.

The EM tracking coils 612 or other localization devices (e.g., FBGs, etc.) can be integrated in the annular cylinder 610 to provide rotation. In this way, the position of the transducers 404 can be tracked, which may include a combination of the catheter/sheath movement and the rotation of the annular cylinder 610. The same construction can be applied to a sheath structure as well. The number of transducers 404 and the number of tracking coils may vary. The catheter or sheath of FIG. 6 preferably comprises a working channel for intervention (stent perforation, cutting tool, ablation, contrast injection, etc.), pressure sensors, temperature and electrical signal sensors, ablation electrodes.

Referring to FIGS. 7A-7D, an illustrative demonstration of how transducers 404 arranged in an array may be employed to determine presence and location of a branching lumen. FIGS. 7A-7D illustratively show a technique in which side branches of a main lumen are found. The configuration is developed in-plane for simplicity of explanation. A background 702 shows an interior surface of a main lumen and a circle 704 shows a view down a branching lumen off the main lumen. The ultrasound transducers 404 are placed on a circumference of the device 106 (e.g., catheter, sheath, etc.).

FIGS. 7A-7D include two columns. A first column 706 simulates what is happening inside a subject while a second column 708 shows a graphical display response to the occurrence in first column 706. In column 706, sequential images of the motion of the device 106 including the transducers 404 with respect to the lumen of the artery are depicted. In column 708, the corresponding situation is displayed on a screen for the physician to support a decision of when to proceed with stent-graft fenestration. Darkened blocks 710 represent that these discrete transducers 404 are within an area of the branching lumen 704. Lighter blocks 712 represent that these discrete transducers 404 are outside an area of the branching lumen 704.

It is preferable that device 106 includes localization, e.g., employs EM, FBG) or other tracking. In this way, the position of the arteries that are found with the ultrasound technique can be registered and the information overlaid on a fluoroscopy image, or a preoperative CT or MRI image. Audible feedback may be employed in accordance with the information received from the transducers 404, e.g., different sounds for different numbers of transducers in alignment with the side-branch may be provided, etc. In addition, blood flow rate and direction for the side-branch may be provided audibly.

As shown, as device 106 passes over the branching lumen 704 in column 706, the transducers 404 over or within the opening of the branching lumen 706 change color, texture, or other visual effect to indicate the presence and position of the lumen 706. Note that the number of transducers 404 can vary.

The information received by the ultrasound transducers 404 is different for different places. For example, in the Abdominal Aortic Aneurysm (AAA) stenting, clear differences are expected between a region of stented aorta (the stent sits onto the aortic wall), the region of a stented neck of the aneurysm, and a region where side branches like renal or iliac arteries are blocked by the stent.

Figure 8A:
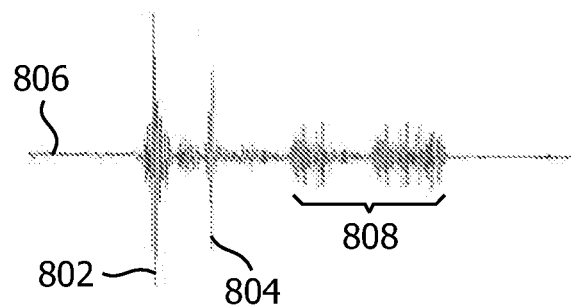
FIGS. 8A-8C show signal response for a plurality of interventional devices and stent positions in accordance with one illustrative embodiment.
Figure 8B:
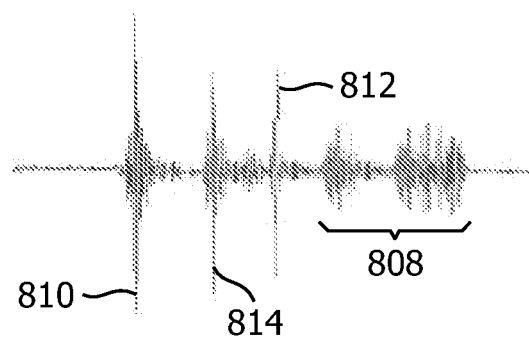
Figure 8C:
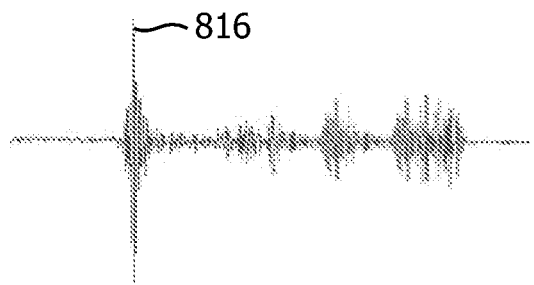

Referring to FIGS. 8A-8C, illustrations of signal response differences are shown in the signals of the discrete ultrasound transducers 404. For example, in FIG. 8A, signals are imaging a region of a stented aorta (the stent sits onto the aortic wall). Signal 802 represents the stent and front wall of the aorta, and signal 804 represents the back wall of the aorta. Signals for blood 806 and for structure beyond the aorta 808 are also shown. In FIG. 8B, the signals are imaging the region of a stented neck of the aneurysm. A signal for the stent 810, the back 812 of the aorta and the front 814 of the aorta are shown. In FIG. 8C, signals 816 imaging the region where side branches like renal or iliac arteries are blocked by the stent are shown.

These signals are interpreted by module 122 of FIG. 1 to indicate, on a display (115, FIG. 1), a position of the transducers 404 relative to internal lumen structures or branches to assist a physician during a procedure. By using the A-line ultrasound signals from the discrete transducers 404 or eventually the M-mode images of the individual transducers when the images are acquired by applying a motion to the device 106 on which the discrete ultrasound images are mounted, 2D or 3D ultrasound images can be constructed. The position of the device 106 is known during the operation, and the motion of the device 106 is recorded and used for the construction of 2D and/or 3D ultrasound images based on the information from the discrete transducers 404.

Figure 9:
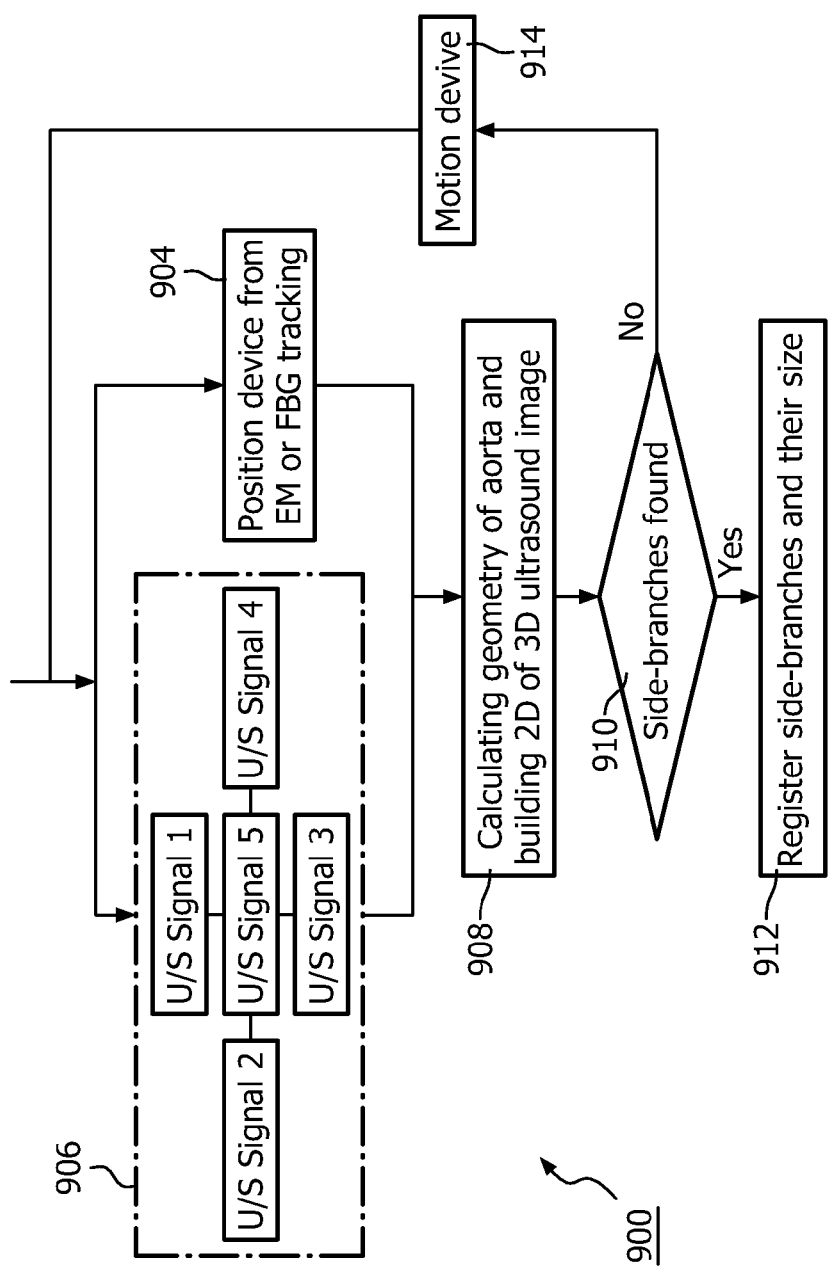
FIG. 9 is a block/flow diagram showing a system/method for determining branches and their location in accordance with an illustrative embodiment.

Referring to FIG. 9, a system/method 900 for constructing ultrasound images is shown. The system/method 900 finds structures such as side branches in an AAA stenting application or other applications. A device configured with one or more ultrasonic transducers is moved into place within a subject. In block 904, a position of the device is obtained using a localization system which may include one or more of EM tracking, FBG tracking, etc. In block 906, ultrasonic transducers of the device are activated and their signals sensed to build an image or provide audible feedback. For example, the device may employ low-resolution transducing or employ an array of transducers, as described above. FIG. 9 illustratively shows ultrasonic signals 1-5 for each of five transducers (404). The positional relationship between the transducers is advantageously employed to more accurately identify a position relative to a branching lumen. In block 908, geometry is computed of an internal structure to build a 2D or 3D ultrasound image. In block 910, a determination of features is made, e.g., were side-branches found? If yes, register the side-branches and their size in an image, e.g., an X-ray image, a CT image or MRI image in block 912. In addition, the blood flow may be monitored by the ultrasound transducers, and audible tones may be provided indicating flow rate and direction for the side branches. If no side-branch is found, move the device in block 914. The motion of the device can be any combination of translation and rotation, regular or irregular.

Note, that this technique may be employed for other applications, such as catheter based procedures, e.g., finding coronary arteries, bronchial branching, etc.

Figure 10:
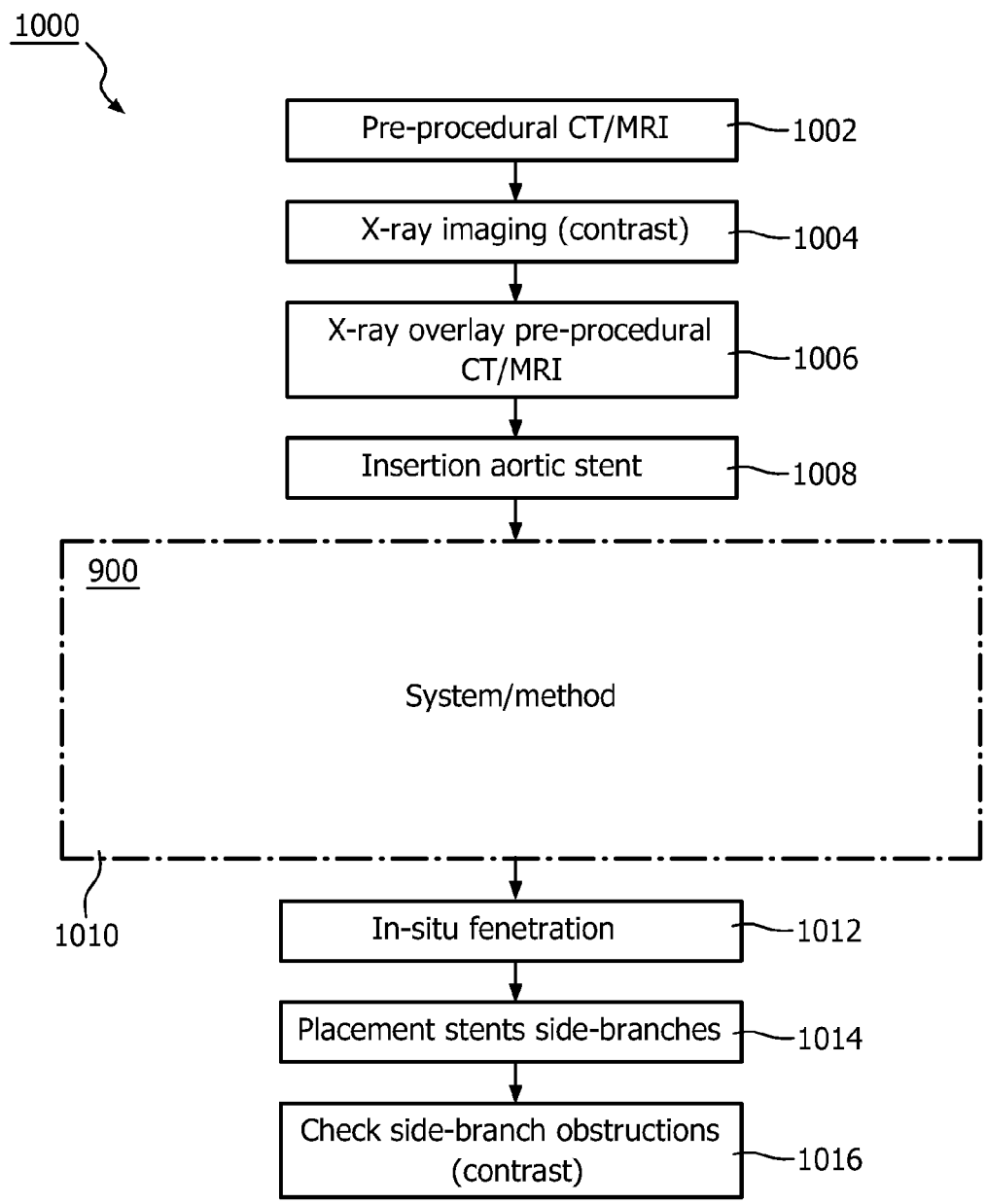
FIG. 10 is a block/flow diagram showing a system/method for performing a procedure such as an AAA procedure in accordance with one embodiment.

Referring to FIG. 10, an illustrative system/method 1000 is illustratively shown for an AAA stenting procedure. This system/method 1000 may be employed for similar procedures as well. In block 1002, a pre-procedural mapping of a subject is performed. This may include MRI, CT or other imaging techniques for providing a mapped volume of the internal region of the procedure. In block 1004, X-ray imaging is performed to provide a real-time image of the area. Contrast may be injected to provide additional resolution of internal structures. In block 1006, an overlay or registration of the X-ray and the pre-procedural image(s) is performed.

In block 1008, a device (e.g., a catheter with ultrasonic transducers, a cutting tool and a stent) is inserted in the subject. The device 106 includes an appliance or appliances such as a stent, graft, etc. In block 1010, structures are identified using the system/method 900 described in FIG. 9. In block 1012, since branching lumen are identified, an in-situ fenestration is possible and is performed. Stents are placed relative to the side branches previously identified (in block 1010) in block 1014. In block 1016, side-branch obstructions are checked using module 122 and visualization system 124. It should be understood that the steps described in FIGS. 9 and 10 may have their order switched, may include additional steps or may be repeated as needed to perform the procedure.

There are various embodiments which can be used for the ultrasound imaging technique with discrete transducers and motion tracking of the device. These techniques can be used in generating 2D and 3D ultrasound images based on information collected by the discrete ultrasound transducers, and taking into account a motion path of the device comprising the transducers using e.g., EM or FBG tracking.

The present embodiments can be applied to the treatment planning of stent-graft fenestrations (of abdominal or thoracic aneurysms), and can also be applied to overlays in which side-branch vessel patency is important, e.g. coronary artery stenting, trans-femoral aortic valve replacement, etc.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems, devices and methods from detection of bifurcations using traceable imaging device and imaging tool (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system, comprising:
   an interventional device including ultrasonic transducers configured to generate a signal to indicate presence of a branch or bifurcation of a lumen inside a subject;
   a localizer configured to track the interventional device in the subject; and
   a processor configured to compare a position of the interventional device against a reference image and to indicate the presence of the branch or bifurcation relative to the position in accordance with the signal for display of indications of the ultrasonic transducers on a screen by changing a visual effect of the displayed indications such that a displayed indication of a first transducer that overlaps the branch or bifurcation is changed to become different from displayed indications of other transducers that do not overlap the branch or bifurcation.

2. The system as recited in claim 1, wherein the interventional device includes one of a catheter and a sheath.

3. The system as recited in claim 2, wherein the one of the catheter and the sheath includes a rotating portion, the rotating portion including at least one of the ultrasonic transducers mounted thereon.

4. The system as recited in claim 1, wherein the ultrasonic transducers include an array of ultrasonic transducers.

5. The system as recited in claim 1, wherein the reference image includes one or more of a real-time image and a preoperative stored image.

6. The system as recited in claim 1, wherein the processor is configured to visually indicate a status of each branch or bifurcation in the reference image.

7. The system as recited in claim 1, wherein the interventional device includes a cutting tool.

8. The system of claim 1, wherein the visual effect includes one of color, texture, shading.

9. The system of claim 1, further comprising a speaker configured to provide a tone in accordance with amount and direction of blood flow in the branch or bifurcation, including providing different sounds for different transducers located in different alignment with the branch or bifurcation.

10. The system of claim 1, wherein the processor is further configured to cause display on the screen of a first column and a second column, the first column including an indication of the of the branch or bifurcation and the indications of the ultrasonic transducers and move the indications of the ultrasonic transducers to simulate movement of the ultrasonic transducers inside the subject, and the second column including further indications of the ultrasonic transducers having different visual effect depending on overlap of the branch or bifurcation with the further indications of the ultrasonic transducers.

11. An interventional device, comprising:
an elongated body having a tip;
a localizer mounted in the tip configured to determine a position of the tip during a procedure;
ultrasonic transducers mounted on or in the elongated body and configured to output a signal to indicate presence of a branch or bifurcation within a lumen and, if present, a position of the branch or bifurcation is determined by a position of the tip as provided by the localizer; and
a processor configured to compare positions of the ultrasonic transducers and to indicate the presence of the branch or bifurcation relative to the positions for display of indications of the ultrasonic transducers on a screen by changing a visual effect of the displayed indications such that a displayed indication of a first transducer that overlaps the branch or bifurcation is changed to become different from displayed indications of other transducers that do not overlap the branch or bifurcation.

12. The device as recited in claim 11, wherein the elongated body comprises one of a catheter and a sheath, and the one of the catheter and the sheath includes a rotating portion, the rotating portion including at least one ultrasonic transducer mounted thereon.

13. The device as recited in claim 11, wherein the elongated body includes a cutting tool.

14. The device of claim 11, further comprising a speaker configured to provide a tone in accordance with amount and direction of blood flow in the branch or bifurcation, including providing different sounds for different transducers located in different alignment with the branch or bifurcation.

15. The device of claim 11, wherein the processor is further configured to cause display on the screen of a first column and a second column, the first column including an indication of the of the branch or bifurcation and the indications of the ultrasonic transducers and move the indications of the ultrasonic transducers to simulate movement of the ultrasonic transducers inside the subject, and the second column including further indications of the ultrasonic transducers having different visual effect depending on overlap of the branch or bifurcation with the further indications of the ultrasonic transducers.

16. A method for determining branching or bifurcation of an internal structure, comprising acts of:
determining a position of an interventional device having ultrasonic transducers in a main lumen using a localizer;
outputting ultrasonic signals from the ultrasonic transducers to construct an ultrasound image of the lumen;
determining a presence and position of a branch or bifurcation relative to the interventional device using the ultrasound signals;
indicating the branches or bifurcations in a reference image;
comparing positions of the ultrasonic transducers relative the position of the branch or bifurcation
indicating the presence of the branch or bifurcation relative to the positions of the ultrasonic transducers; and
displaying indications of the ultrasonic transducers on a screen by changing a visual effect of the displayed indications such that a displayed indication of a first transducer that overlaps the branch or bifurcation is chanced to become different from displayed indications of other transducers that do not overlap the branch or bifurcation.

17. The method as recited in claim 16, wherein the reference image includes an X-ray image and the method further comprises updating the X-ray image and a status in real-time.

18. The method as recited in claim 16, further comprising an act of registering a preoperative image to the reference image.

19. The method of claim 16, further comprising controlling a speaker to provide a tone in accordance with amount and direction of blood flow in the branch or bifurcation, including providing different sounds for different transducers located in different alignment with the branch or bifurcation.

20. The method of claim 16, further comprising an act of displaying on the screen of a first column and a second column, the first column including an indication of the of the branch or bifurcation and the indications of the ultrasonic transducers and move the indications of the ultrasonic transducers to simulate movement of the ultrasonic transducers inside the subject, and the second column including further indications of the ultrasonic transducers having different visual effect depending on overlap of the branch or bifurcation with the further indications of the ultrasonic transducers.

* * * * *